United States Patent [19]

Azuma et al.

[11] Patent Number: 4,755,209
[45] Date of Patent: Jul. 5, 1988

[54] CERTAIN HERBICIDAL 2-PYRIDYLOXY(OR PHENOXY)-PHENOXY-LOWER ALKANOYLAMINOMETHYLENE-PHOSPHONIL ACIDS OR ESTERS THEREOF

[75] Inventors: Shizuo Azuma; Toshiyuki Hiramatsu; Koji Nakagawa, all of Iwakuni; Yataro Ichikawa, Tokorozawa, all of Japan

[73] Assignee: Teijin Limited, Osaka, Japan

[21] Appl. No.: 848,118

[22] Filed: Apr. 4, 1986

[30] Foreign Application Priority Data

Dec. 24, 1985 [JP] Japan .................................. 60-289435

[51] Int. Cl.⁴ .......................... C07F 9/40; C07F 9/58; A01N 43/40; A01N 57/06
[52] U.S. Cl. ........................................... 71/86; 71/94; 546/24; 558/174; 558/168
[58] Field of Search ................... 546/24; 558/168, 174, 558/166; 71/86

[56] References Cited

U.S. PATENT DOCUMENTS 4,618,358 10/1986 Maier ........................................ 71/86
4,627,870 12/1986 Nagubandi ............................... 71/86

Primary Examiner—Alan L. Rotman
Attorney, Agent, or Firm—Wenderoth, Lind & Ponack

[57] ABSTRACT

A phenoxyalkanoylaminomethylphosphonic acid represented by the following formula (I)

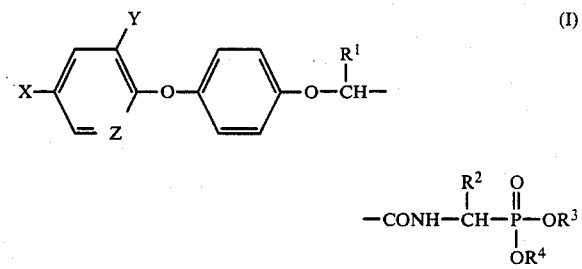

wherein X and Y are identical or different and each represents a hydrogen atom, a halogen atom, CF₃ or an alkyl group having not more than 5 carbon atoms, Z represents CH or N, and R¹, R², R³ and R⁴ are identical or different and each represents a hydrogen atom or a lower alkyl group having 1 to 5 carbon atoms. The compound is useful, as a herbicide, for eradicating weeds, especially narrow-leaved weeds.

8 Claims, No Drawings

CERTAIN HERBICIDAL 2-PYRIDYLOXY(OR PHENOXY)-PHENOXY-LOWER ALKANOYLAMINOMETHYLENE-PHOSPHONIL ACIDS OR ESTERS THEREOF

This invention relates to a phenoxyalkanoylaminomethylphosphonic acid and a herbicide comprising it as an active ingredient. More specifically, this invention pertains to phenoxyalkanolaminomethylphosphonic acids which have selective herbicidal activity and selectively eradicate narrow-leaved weeds without killing narrow-leaved crop plants such as corn and rice.

Herbicides of the type which selectively kills broad-leaved weeds, typified by 2,4-dichlorophenoxyacetic acid, are known as selective herbicidally active compounds. The selectivity of the herbicidal activity of 2,4-dichlorophenoxyacetic acid is between narrow-leaved plants including crop plants and weeds and broad-leaved plants including crop plants and weeds. It is known that 2,4-dichlorophenoxyacetic acid has very little or no activity against narrow-leaved plants [see, for example, Nature, Vol. 155, page 498 (1945)]. It is known on the other hand that compounds resulting from introduction of a chloro- or trifluoromethyl-substituted phenoxy group or a chloro- or trifluoromethyl-substituted pyridyloxy group into the aromatic group of the above compound have the activity of selectively killing narrow-leaved plants.

Japanese Laid-Open Patent Publication No. 44631/1976 discloses a herbicide comprising alpha-[4-(4-trifluoromethylphenoxy)phenoxy]propionic acid, an alpha-[4-(monohalogen-substituted-4-trifluoromethylphenoxy)phenoxy]propionic acid, or a derivative thereof. This patent document specifically discloses only some alkyl esters, alkoxyalkyl esters, chloro phenyl esters, benzyl esters, amilids, acid chlorides and thioesters of the above compounds as the derivative. As shown in Table 5, for example, of this patent document, these compounds do not inhibit growth of broad-leaved plants, whether weeds or crops, but kill narrow-leaved plants such as beer barley, wheat, corn, millet, crabgrass and barnyard grass.

Japanese Laid-Open Patent Publication No. 125626/1977 discloses a herbicide comprising as an active ingredient a compound represented by the following formula

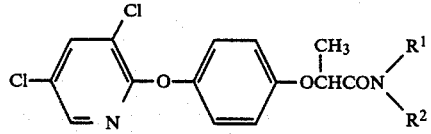

wherein $R^1$ is hydroxy, hydroxyalkyl, lower alkoxy, lower alkenyloxy, acyl, amino, aralkyl, chloroaralkyl, $-R^3-COOR^4$ (where $R^3$ is lower alkylene, and $R^4$ is hydrogen, lower alkyl or a salt-forming atom or radical), or

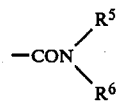

(where $R^5$ and $R^6$ are hydrogen, lower alkyl or lower alkoxy); $R^2$ is hydrogen, lower alkyl, lower alkoxy, hydroxyalkyl, phenyl, or chlorophenyl; and

may be

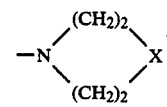

(where X ix is methylene or oxygen). This patent document states that the above compound hardly affects broad-leaved plants, but kill narrow-leaved plants such as barnyard grass.

Japanese Laid-Open Patent Publication No. 15,825/1977 discloses a herbicide comprising as an active ingredient a compound represented by the following formula

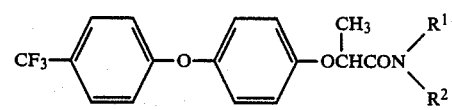

wherein $R^1$ is $-R^3-COO^4$ (where $R^3$ and $R^4$ are the same as defined above), hydroxyalkyl, $-COR^5$ (where $R^5$ is lower alkyl or cycloalkyl),

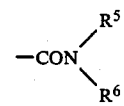

(where $R^6$ and $R^7$ are hydrogen, lower alkyl or lower alkoxy), or an aralkyl or heterocyclic group which may be substituted by at least one of halogens and lower alkyl or alkoxy groups; $R^2$ is hydrogen, lower alkyl, or phenyl which may be substituted by at least one of halogens and lower alkyl or alkoxy groups; and

may be

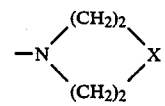

(where X is O or $CH_2$). This patent document states that the above compound hardly affects broad-leaved plants such as radish and soybeans, but shows strong activity against barnyard grass and crabgrass.

Japanese Laid-Open Patent Publication No. 2438/1978 discloses a compound of the following formula

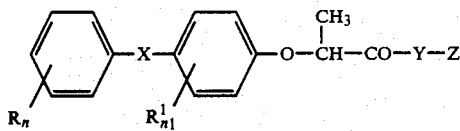

wherein R and R¹ represent halogen, $C_{1-4}$ haloalkyl, $C_{1-4}$ alkyl, nitro, $C_{1-4}$ alkoxy, or $C_{1-4}$ alkylthio, n and $n_1$ are integers of 0 to 3, X is —O— or —$CH_2$—, Y is O, S or NH, Z is cyanoethyl or

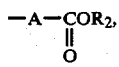

A is a methylene group substituted by $CH_3$, $C_2H_5$, $COCH_3$ or another radical represented by $COOR_3$ or a phenyl group mono- or di-substituted by $C_{1-4}$, halogen and/or nitro, and $R^3$ is $C_{1-4}$ alkyl, and a herbicide comprising the above compound as an active ingredient. This patent document states that the above compound controls gramineous weeds such as Avena, Alopecurus, Lolium, Setaria, Echinocloa and Digitaria.

Japanese Patent Publication No. 8727/1979 describes a herbicide comprising as an active ingredient a compound of the following formula

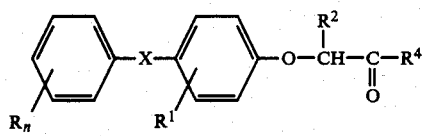

wherein R is halogen, $C_{1-4}$ alkyl, $C_{1-4}$ alkoxy or $C_{1-4}$ alkylthio, $R^1$ is H, halogen or $C_{1-4}$ alkyl, n is an integer of 1 to 3, $R^2$ is H, $C_{1-10}$ alkyl or $C_{2-6}$ alkoxyalkyl, and $R^4$ is OH, $C_{1-10}$ alkoxy, trichloroethyloxy, $C_{1-6}$ alkylthio, $C_{2-6}$ alkenyloxy, cyclohexyloxy, methylcyclohexyloxy, phenoxy substituted by one or two halogens, phenylthio which may be substituted by one or two halogens, alkylamino in which the alkyl has 1 to 4 carbon atoms, dialkylamino or

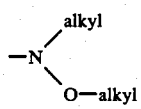

in which the alkyl has 1 to 4 carbon atoms, phenylamino substitued by halogen, $CF_3$, —$OCF_2CF_2H$ or —$COOCH_3$, or —O—Kat where Kat is an inorganic or organic base cation. This patent document states that the abobve herbicide has an outstanding selective herbicidal action on gramineous weeds.

European Laid-Open Patent Publication No. 0138158 describes a compound of the following formula

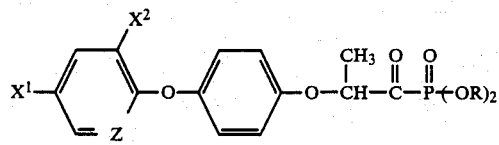

wherein $X^1$ is halogen or $CF_3$, $X^2$ is H, halogen or $CF_3$, Z is N, CH, or CCl, and R is alkyl or haloalkyl, as a total or selective herbicide for use against, for example, mono- and di-cotyledonous weeds in perennial crops or for pre- or post-emergence use against grassy weeds in cultures such as beet, cotton, soya, potatoes and cereals.

German Laid-Open Patent Publication No. 3402982 (Japanese Laid-Open Patent Publication No. 163891/1985) describes phenoxypropionyloxyalkanephosphonates of the following formula

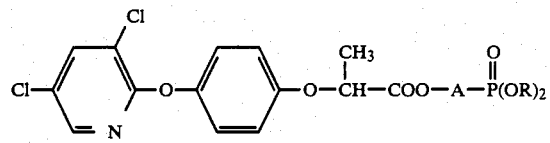

wherein R is alkyl which may be substituted and A is alkanediyl which may be substituted. This patent document discloses that these compounds are effective for killing broad-leaved or narrow-leaved weeds.

It is an object of this invention therefore to provide novel phenoxyalkanoylaminomethylphosphonic acids.

Another object of this invention is to provide a selective herbicide having selective herbicidal activity.

Another object of this invention is to provide a selective herbicide which selectively kills narrow-leaved weeds without substantially inhibiting the growth of broad-leaved plants and substantially affecting useful narrow-leaved plants.

Another object of this invention is to provide selective herbicidal compounds which eradicate narrow-leaved weeds without substantially causing phytotoxicity to useful crop plants, particularly broad-leaved crops such as soybean, cotton, sunflower and beet and narrow-leaved crops such as corn and wheat and therefore without substantially inhibiting the growth of these useful plants; and herbicides containing the aforesaid compounds.

Another object of this invention is to provide compounds which kill many narrow-leaved plants or inhibit their growth without causing substantial phytotoxicity to narrow-leaved crops such as rice, corn and wheat and various broad-leaved crops, and therefore when applied to a locus where the aforesaid useful crops and hazardous weeds grow together, can create a condition in which the useful crops easily grow beyond the growth of the weeds.

Another object of this invention is to provide a selective herbicide applicable by foliar spraying and soil treatment, which can kill, or inhibit the growth of, weeds by application to their foliage, and also can inhibit the emergence of weeds without substantially inhibiting the emergence of useful crops by application to the soil before emergence.

Another object of this invention is to provide a selective herbicide which has low toxicity to animals and fish and remains little in the soil.

Another object of this invention is to provide a method of eradicating weeds by using the aforesaid compounds or herbicides of this invention.

Further objects of this invention along with its advantages will become apparent from the following description.

According to this invention, the objects and advantages of this invention are achieved by a phenoxyalkanoylaminomethylphosphonic acid represented by the following formula (I)

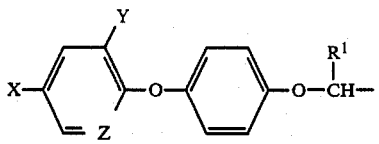

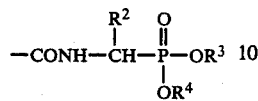

wherein X and Y are identical or different and each represents a hydrogen atom, a halogen atom, CF₃ or an alkyl group having not more than 5 carbon atoms, Z represents CH or N, and R¹, R², R³ and R⁴ are identical or different and each represents a hydrogen atom or a lower alkyl group having 1 to 5 carbon atoms.

In formula (I), X and Y are identical or different, and each represents a hydrogen atom, a halogen atom, CF₃ or an alkyl group having not more than 5 carbon atoms. The halogen atom is, for example, fluorine, chlorine or bromine. The alkyl group having not more than 5 carbon atoms may be linear or branched, and includes, for example, methyl, ethyl, n-propyl, iso-propyl, n-butyl, sec-butyl, iso-butyl, t-butyl and n-pentyl.

In formula (I), at least one of X and Y is preferably a halogen atom, CF₃ or an alkyl group having not more than 5 carbon atoms.

Z is CH or N, and the compounds of formula (I) may be divided into the following groups according to the definition of Z for the sake of convenience.

Compounds of formula (I) in which Z is CH are represented by the following formula

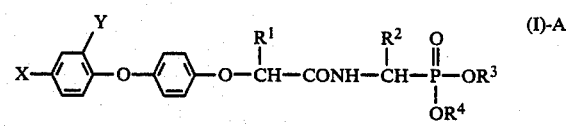

wherein X, Y, R¹, R², R³ and R⁴ are as defined above.

Compounds of formula (I) in which Z is N are represented by the following formula

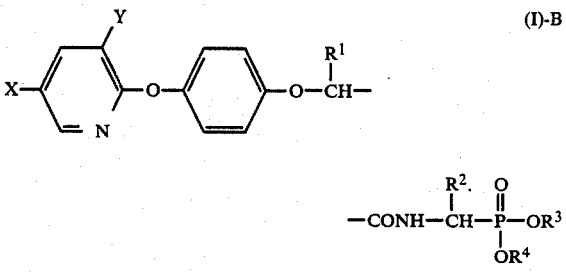

wherein X, Y, R¹, R², R³ and R⁴ are as defined above.

In formula (I) [including formulae (I)-A and (I)-B throughout the specification], R¹, R², R₃ and R⁴ are identical or different, and each represents a hydrogen atom or a lower alkyl group having 1 to 5 carbon atoms. Specific examples of the alkyl group having 1 to 5 carbon atoms are the same as cited above for X and Y.

R¹ is preferably a hydrogen atom or a methyl group, especially the methyl group. R² is preferably a hydrogen atom or a methyl group. R³ and R⁴ are preferably a methyl, ethyl, propyl or butyl group.

Specific examples of the phenoxyalkanoylaminomethylphosphonic acids of formula (I) are given below.

Compounds of formula (I)-A (100) 4-(2-chloro-4-trifluoromethylphenoxy)phenoxy acetylaminomethylphosphonic acid diethyl ester,
(102) 2-[4-(2-chloro-4-trifluoromethylphenoxy)phenoxy]-propionylaminomethylphosphonic acid diethyl ester,
(104) 2-[4-(2-chloro-4-trifluoromethylphenoxy)phenoxy]propionylaminoethylphosphonic acid di-n-butyl ester,
(105) 2-[4-(4-trifluoromethyl)phenoxy]phenoxypropionyl-1-aminoethylphosphonic acid diethyl ester,
(106) 4-(4-trifluoromethylphenoxy)phenoxyacetylaminomethylphosphonic acid diethyl ester,
(108) 2-[4-(4-trifluoromethylphenoxy)phenoxy]propionylaminomethylphosphonic acid diethyl ester,
(110) 2-[4-(4-trifluoromethylphenoxy)phenoxy]propionylaminomethylphosphonic acid di-n-butyl ester,
(111) 2-[4-(4-trifluoromethyl)phenoxy]phenoxypropionyl-1-aminopropylphosphonic acid diethyl ester,
(112) 2-[4-(2-chloro-4-trifluoromethylphenoxy)phenoxy]propionylaminomethylphosphonic acid,
(114) 2-[4-(4-bromo phenoxy)phenoxy]propionylaminomethyl phosphonic acid diether ester,
(116) 2-[4-(4-chloro phenoxy)phenoxy]propionylaminomethyl phosphonic acid diether ester,
(118) 2-[4-(2,4-dichloro phenoxy)phenoxy]propionylaminomethyl phosphonic acid diether ester,
(120) 2-[4-(2-chloro-4-methyl phenoxy)phenoxy]propionylaminomethyl phosphonic acid diether ester.

Compounds of formula (I)-B (200) 4-(3-chloro-5-trifluoromethyl-pyridine-2-yloxy)-phenoxy acetylaminomethylphosphonic acid diethyl ester,
(202) 2-[4-(3-chloro-5-trifluoromethylpyridine-2-yloxy)phenoxy]propionylaminomethyl phosphonic acid diethyl ester,
(203) 2-[4-(3-chloro-5-trifluoromethyl-pyridine-2-yloxy)phenoxy]propionyl-1-aminoethyl phosphonic acid diethyl ester,
(204) 2-[4-(3-chloro-5-trifluoromethyl-pyridine-2-yloxy)phenoxy]propionylaminomethyl phosphonic acid diethyl ester,
(205) 2-[4-(3-chloro-5-trifluoromethyl-pyridine-2-yloxy)phenoxy]propionyl-1-aminopropyl phosphonic acid diethyl ester,
(206) 4-(5-trifluoromethyl-pyridine-2-yloxy)phenoxyacetylaminomethyl phosphonic acid diethyl ester,
(208) 2-[4-(5-trifluoromethyl-pyridine-2-yloxy)phenoxy]propionylaminomethyl phosphonic acid diethyl ester,
(210) 2-[4-(5-trifluoromethyl-pyridine-2-yloxy)phenoxy]propionylaminomethyl phosphonic acid di-n-butyl ester,
(212) 4-(3-trifluoromethyl-pyridine-2-yloxy)phenoxyacetylaminomethyl phosphonic acid diethyl ester,
(214) 2-[4-(3-trifluoromethyl-pyridine-2-yloxy)phenoxy]propionylaminomethyl phosphonic acid diethyl ester.

The compounds of formula (I) can be produced, for example, by process 1 or process 2 shown by the following reaction scheme.

Process 1

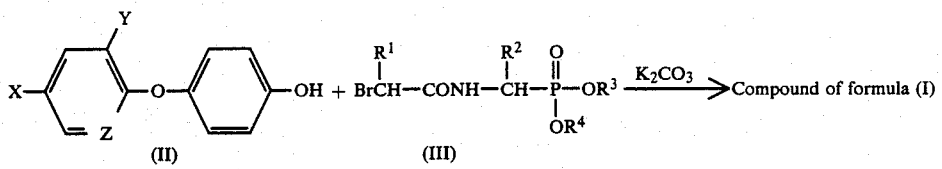

Process 2

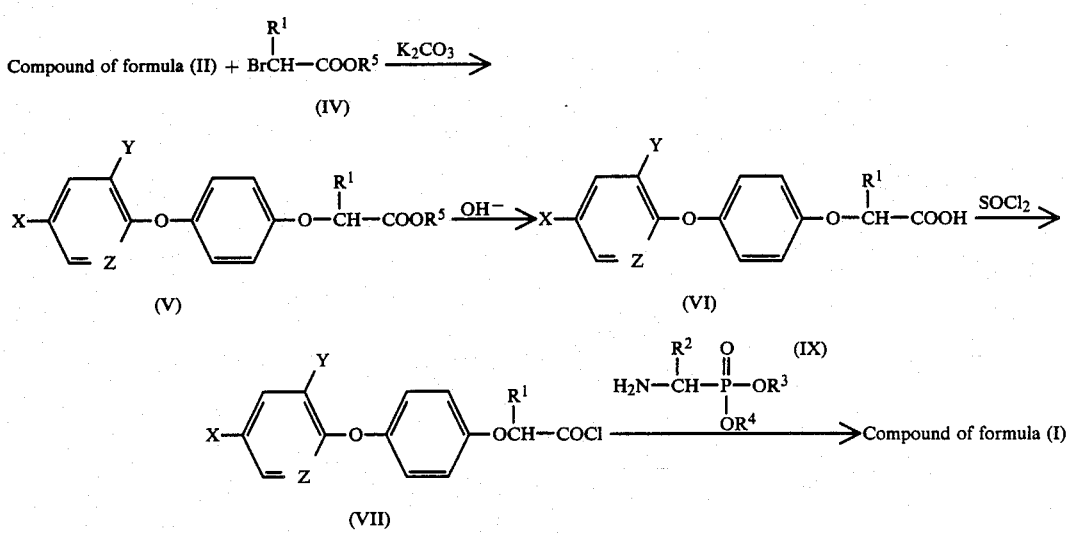

In formulae (II) to (IX) above, X, Y, Z, $R^1$, $R^2$ and $R^3$ are as defined above. $R^5$ in formulae (IV) and (V) represents an alkyl group having 1 to 5 carbon atoms.

The steps in each of processes 1 and 2 are carried out by methods known per se. When it is desired to obtain a compound of formula (I) in which $R^3$ and $R^4$ are hydrogen atoms by process 2, the above reaction is carried out by using a compound of formula (IX) in which $R^3$ and $R^4$ are hydrogen atoms; or the reaction is carried out by using a compound of formula (IX) in which $R^3$ and $R^4$ are alkyl groups having 1 to 5 carbon atoms to give a compound of formula (I) in which $R^3$ and $R^4$ are the corresponding lower alkyl groups, and the resulting compound (I) is hydrolyzed.

The phenoxyalkanoylaminomethylphosphonic acids of formula (I) have the property of affecting the metabolism of plants to inhibit the growth of a certain kind of plants, regulate the growth of a certain kind of plants, dwarf a certain kind of plants, or to kill a certain kind of plants.

The compounds of formula (I) provided by this invention show selective herbicidal activity, and particularly have the marked property of selectively killing narrow-leaved weeds without substantially inhibiting the growth of broad-leaved plants and substantially affecting narrow-leaved useful plants.

Accordingly, the present invention also provides a herbicide comprising the phenoxyalkanoylaminomethylphosphonic acid of formula (I) as a herbicidally active ingredient.

The compounds of formula (I) provided by this invention can also be applied to seeds of plants, and to plants in various growth stages through foliage or roots. In other words, the compounds of this invention, either as such or as a composition, are applied to plants whose growth is to be inhibited, namely plants whose metabolism is to be regulated, seeds of such plants, a locus where such plants are growing, or a locus where the growth of such plants is anticipated, in amounts sufficient to regulate the metabolism of the plants.

The metabolism of plants can be regulated by applying the compounds of this invention at a rate of 1 g to 2 kg, preferably 5 g to 1 kg, especially preferably 10 g to 200 g, per 10 ares.

When it is desired to inhibit the growth of, or eradicate, hazardous plants by the compounds of this invention, the compounds, either as such or as a composition, can be applied directly to the plants or their seeds or to the soil in amounts sufficient to inhibit the growth of, or eradicate, the plants in a locus where beneficial plants or their seeds and the hazardous plants or their seeds are growing together or are likely to grow together.

The hazardous plants may be defined as plants which come into an environment created by man, such as a paddy or an upland farm, from the sorrounding nature, and grow there and which are considered by man to be useless in that environment or do harm to it. Such hazardous plants are generally called weeds. Examples of the weeds to which the compounds of this invention are to be applied are shown below.

Gramineae

*Sorghum halepense,*
*Avena fatua,*
*Digitaria adscendens Henr.,*
*Setaria faberi,*
*Agropyron repens,*
*Panicum texanum,*
*Echinochloa crus-galli,*
*Setaria viridis,*

*Poa annua,*
*Eleusine indica,*
*Axonopus affinis,*
*Bachiaria platyphylla,*
*Bromus tectorum,*
Cynodon dactylon,
Panicum dichotomiflorum,
*Paspalum dilatatum,*
*Echiochloa colona,*
*Panicum capillare,* and
*Setaria lutescens.*

Amaranthaceae

*Amaranthus retroflexas L.,* and
*Amaranthus lividus Loise I.*

Compositae

*Erigeron annuus L.*

The beneficial plants in the above case are, for example, plants producing cereals, and lawns. Since the compounds of this invention exert little or no adverse effect on the growth of not only various broad-leaved plants such as soybean, cotton, sunflower and beet but also narrow-leaved crops such as rice, corn and wheat, they are very suitable for application to paddies and upland farms for cultivating these plants. By applying the compounds of this invention to a locus where lawns are growing, the emergence and growth of weeds can be inhibited.

In some cases, it is desirable to apply the compounds of this invention while hazardous plants do not grow so much, particularly while the height of the hazardous plants is lower, or a little bit higher, than the height of beneficial plants.

When weeds are to be eradicated by using the compounds of this invention, the compounds can be applied either as such or as a composition to weeds to be eradicated, their seeds, or a locus where such weeds are growing, or are likely to grow, for example in a crop cultivating area, in amounts sufficient for eradication.

The herbicide of this invention shows a very good effect against narrow-leaved weeds and also exhibits herbicidal activity against broad-leaved weeds of small heights. When used in dosages which exhibit this effect, the herbicide does not substantially injure the aforesaid useful crops.

A group of preferred compounds of formula (I) which have especially good selective herbicidal activity are expressed by the following formula (I)-1

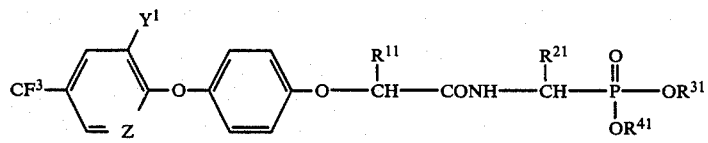

(I)-1 wherein Z is as defined above, $Y^1$ represents H or Cl, $R^{11}$ and $R^{11}$ are identical or different and each represents H or $CH_3$, and $R^{31}$ and $R^{41}$ are identical or different and each represents an alkyl group having 1 to 4 carbon atoms.

The compounds of this invention can be used in usual formulations such as a solution, an emulsifiable concentrate, a suspension, a dust, a paste or granules.

Such formulations are prepared by using at least one agriculturally acceptable diluent. Examples include solid carriers such as talc, bentonite, clay, kaolin, diatomaceous earth, white carbon, vermiculite, slaked lime, ammonium sulfate and urea; liquid carriers such as water, alcohols, dioxane, acetone, xylene, cyclohexane, methylnaphthalene, dimethylformamide, N-methylpyrrolidone, dimethyl sulfoxide, cyclohexanone, methyl ethyl ketone and methyl isobutyl ketone; surface-active agents, emulsifiers or dispersants such as alkylsulfuric acid esters, alkylsulfonic acid salts, ligninsulfonic acid salts, polyoxyethylene glycol ethers, polyoxyethylene alkylaryl ethers, polyoxyethylene sorbitan monoalkylates and dinaphthylmethanedisulfonic acid salts; and various adjuvants such as carboxylmethyl cellulose and gum arabic.

For example, such a formulation can be prepared by mixing the compound of this invention with the aforesaid carrier and/or emulslifier, etc.

The compound of this invention may be present in a proportion of usually 0.01 to 99% by weight, preferably 0.1 to 95% by weight, in the formulation.

The compound of this invention, as such or in admixture with another active compound or as the aforesaid formulation, can be applied to plants by usual methods such as spraying, atomizing, or dusting.

The following examples illustrate the present invention in greater detail.

In these examples, parts are by weight unless otherwise specified. The herbicidal activity of the active test compounds was evaluated on a scale of 0 to 5 in which 0 means that the plants were as sound as before the application of the active compound and 5 means that the application of the active compound caused the plants to wither and die, and 1, 2, 3 and 4 mean varying degrees of the enfeebled state of the plants between 0 and 5.

Production Examples

EXAMPLE 1

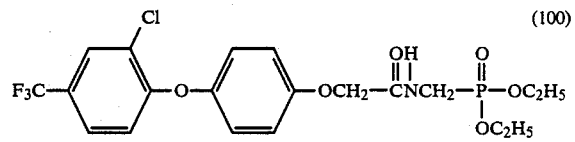

(100)

1.44 parts of 4-(2-chloro-4-trifluoromethylphenoxy)-phenol, 0.84 part of ethyl bromoacetate, and 1.38 parts of anhydrous potassium carbonate were refluxed for 3 hours in 20 parts by volume of methyl ethyl ketone in an atmosphere of nitrogen. After the reaction, the reaction mixture was filtered. The filtrate was concentrated, and water was added. The mixture was then extracted with ethyl acetate. The extract was washed with a 1N aqueous solution of sodium hydroxide and then with water, and dried over anhydrous sodium sulfate. The solvent was removed under reduced pressure to give 1.5 parts of ethyl 4-(2-chloro-4-trifluoromethylphenoxy)phenoxyacetate.

Two parts by volume of ethanol and 4 parts by volume of water were added to the resulting acetate, and 7.8 parts by volume of 1N-KOH was added dropwise. The mixture was stirred at room temperature for 3 hours. After the reaction, ethanol was removed under reduced pressure, and water was added. The mixture was washed with ether. The aqueous layer was acidified with hydrochloric acid, extracted with ethyl acetate, washed with water, and then dried over anhydrous sodium sulfate. The solvent was removed under reduced pressure to give 1.2 parts of 4-(2-chloro-4-trifluoromethylphenoxy)phenoxyacetic acid. The resulting phenoxyacetic acid (0.21 part) and 0.14 part of thionyl chloride were reacted at 80° C. for 3 hours. After the reaction, the excess of thionyl chloride was removed under reduced pressure to give 0.22 part of 4-(2-chloro-4-trifluoromethylphenoxy)phenoxyacetyl chloride. The resulting phenoxyacetyl chloride was added dropwise under ice cooling to a mixture consisting of 0.1 part of diethylaminomethyl phosphonate, 0.067 part of triethylamine and 5 parts by volume of benzene. After the addition, the mixture was stirred for 3 hours at room temperature. Water was added, and the mixture was extracted with benzene. The extract was washed with saturated aqueous sodium bicarbonate solution and water, and dried over anhydrous sodium sulfate. The solvent was removed under reduced pressure to give 0.27 part of the desired compound (100). The IR and NMR spectral data of the compound are shown in Table 1.

EXAMPLES 2-23

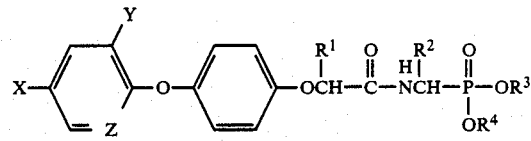

By the same method as in Example 1, compounds (102) to (214) of the above formula in which X, Y, Z, $R^1$, $R^2$, $R^3$ and $R^4$ are as shown in Table 1 were synthesized. The IR and NMR spectral data of these compounds are shown in Table 1.

TABLE 1

| Example | Compound No. | X | Y | Z | $R^1$ | $R^2$ | $R^3$ | $R^4$ | IR $\nu$(cm$^{-1}$) | NMR in CDCl$_3$ $\delta$(ppm) |
|---|---|---|---|---|---|---|---|---|---|---|
| 1 | (100) | —CF$_3$ | Cl | =CH— | H | H | —C$_2$H$_5$ | —C$_2$H$_5$ | 3300<br>1670<br>1490<br>1320<br>1240<br>1120 | 1.33(6H)<br>3.63-3.93(2H)<br>3.93-4.33(4H)<br>4.53(2H)<br>6.80-7.70(8H) |
| 2 | (102) | —CF$_3$ | Cl | =CH— | —CH$_3$ | H | —C$_2$H$_5$ | —C$_2$H$_5$ | 3250<br>1670<br>1490<br>1320<br>1230<br>1120 | 1.13-1.43(6H)<br>1.58(3H)<br>3.57-3.87(2H)<br>3.80-4.27(4H)<br>4.70(1H)<br>6.80-7.70(8H) |
| 3 | (104) | —CF$_3$ | Cl | =CH— | —CH$_3$ | H | —C$_4$H$_9$ | —C$_4$H$_9$ | 3250<br>1670<br>1490<br>1320<br>1230<br>1120 | 0.80-1.07(6H)<br>1.17-1.80(8H)<br>1.60(3H)<br>3.57-3.87(2H)<br>3.83-4.23(4H)<br>4.70(1H) 6.80-7.70(8H) |
| 4 | (105) | —CF$_3$ | H | =CH— | —CH$_3$ | —CH$_3$ | —C$_2$H$_5$ | —C$_2$H$_5$ | 3250<br>1680<br>1500<br>1325<br>1230<br>1120 | 1.10-1.50(9H)<br>1.58 (3H)<br>3.83-4.20(5H)<br>4.65(1H)<br>6.40-6.90(1H)<br>6.80-7.50(8H) |
| 5 | (106) | —CF$_3$ | H | =CH— | H | H | —C$_2$H$_5$ | —C$_2$H$_5$ | 3300<br>1670<br>1490<br>1320<br>1220<br>1120 | 1.33(6H)<br>3.63-3.93(2H)<br>3.93-4.33(4H)<br>4.53(2H)<br>6.83-7.63(9H) |
| 6 | (108) | —CF$_3$ | H | =CH— | —CH$_3$ | H | —C$_2$H$_5$ | —C$_2$H$_5$ | 3250<br>1670<br>1500<br>1320<br>1220<br>1120 | 1.13-1.43(6H)<br>1.60(3H)<br>3.57-3.87(2H)<br>3.83-4.27(4H)<br>4.67(1H)<br>6.73-7.60(9H) |
| 7 | (110) | —CF$_3$ | H | =CH— | —CH$_3$ | H | —C$_4$H$_9$ | —C$_4$H$_9$ | 3250<br>1670<br>1490<br>1320<br>1220<br>1120 | 0.77-1.10(6H)<br>1.10-1.80(8H)<br>1.60(3H)<br>3.60-3.90(2H)<br>3.83-4.27(4H)<br>4.70(1H) 6.73-7.63(9H) |
| 8 | (111) | —CF$_3$ | H | =CH— | —CH$_3$ | —CH$_2$CH$_3$ | —C$_2$H$_5$ | —C$_2$H$_5$ | 3240<br>1670<br>1500<br>1320 | 0.80-1.67(14H)<br>3.80-4.40(5H)<br>4.70(1H)<br>6.30-6.70(1H) |

TABLE 1-continued

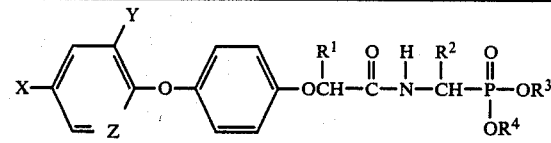

| Example | Compound No. | X | Y | Z | R¹ | R² | R³ | R⁴ | IR ν(cm⁻¹) | NMR in CDCl₃ δ(ppm) |
|---|---|---|---|---|---|---|---|---|---|---|
| | | | | | | | | | 1225 | 6.80–7.70(8H) |
| | | | | | | | | | 1120 | |
| 9 | (112) | —CF₃ | Cl | =CH— | —CH₃ | H | H | H | 3250 | 1.60(3H) |
| | | | | | | | | | 2500–2800 | 3.60–3.90(2H) |
| | | | | | | | | | 1670 | 4.70(1H) |
| | | | | | | | | | 1490 | 6.77–7.70(10H) |
| | | | | | | | | | 1320 | |
| | | | | | | | | | 1230 | |
| 10 | (114) | Br | H | =CH— | —CH₃ | H | —C₂H₅ | —C₂H₅ | 3250 | 1.17–1.47(6H) |
| | | | | | | | | | 1670 | 1.60(3H) |
| | | | | | | | | | 1500 | 3.57–3.87(2H) |
| | | | | | | | | | 1480 | 3.87–4.27(4H) 4.67(1H |
| | | | | | | | | | 1220 | 6.70–7.43(9H) |
| | | | | | | | | | 1020 | |
| 11 | (116) | Cl | H | =CH— | —CH₃ | H | —C₂H₅ | —C₂H₅ | 3250 | 1.13–1.43(6H) |
| | | | | | | | | | 1670 | 1.57(3H) |
| | | | | | | | | | 1500 | 3.57–3.87(2H) |
| | | | | | | | | | 1480 | 3.83–4.27(4H) |
| | | | | | | | | | 1220 | 4.63(1H) |
| 12 | (118) | Cl | Cl | =CH— | —CH₃ | H | —C₂H₅ | —C₂H₅ | 3250 | 1.13–1.43(6H) |
| | | | | | | | | | 1670 | 1.57(3H) |
| | | | | | | | | | 1500 | 3.57–3.87(2H) |
| | | | | | | | | | 1470 | 3.87–4.33(4H) |
| | | | | | | | | | 1230 | 4.67(1H) |
| | | | | | | | | | 1030 | 6.70–7.43(8H) |
| 13 | (120) | —CH₃ | Cl | =CH— | —CH₃ | H | —C₂H₅ | —C₂H₅ | 3300 | 1.13–1.43(6H) |
| | | | | | | | | | 1670 | 1.57(3H) |
| | | | | | | | | | 1500 | 2.23(3H) |
| | | | | | | | | | 1200 | 3.57–3.87(2H) |
| | | | | | | | | | | 3.87–4.37(4H) |
| | | | | | | | | | | 4.63(1H) |
| | | | | | | | | | | 6.53–7.33(8H) |
| 14 | (200) | —CF₃ | Cl | =N— | H | H | —C₂H₅ | —C₂H₅ | 3280 | 1.33(6H) |
| | | | | | | | | | 1670 | 3.63–3.93(2H) |
| | | | | | | | | | 1500 | 3.90–4.37(4H) |
| | | | | | | | | | 1460 | 4.53(2H) |
| | | | | | | | | | 1320 | 6.73–7.27(5H) |
| | | | | | | | | | 1190 | 7.90–8.23(2H) |
| 15 | (202) | —CF₃ | Cl | =N— | —CH₃ | H | —C₂H₅ | —C₂H₅ | 3250 | 1.10–1.38(6H) |
| | | | | | | | | | 1670 | 1.60(3H) |
| | | | | | | | | | 1500 | 3.57–3.87(2H) |
| | | | | | | | | | 1460 | 3.93–4.37(4H) |
| | | | | | | | | | 1320 | 4.70(1H) |
| | | | | | | | | | 1190 | 6.67–7.27(5H) |
| | | | | | | | | | | 7.90–8.23(2H) |
| 16 | (203) | —CF₃ | Cl | =N— | —CH₃ | —CH₃ | —C₂H₅ | —C₂H₅ | 3250 | 1.05–1.50(9H) |
| | | | | | | | | | 1675 | 1.60(3H) |
| | | | | | | | | | 1500 | 3.80–4.30(5H) |
| | | | | | | | | | 1460 | 4.63(1H) |
| | | | | | | | | | 1320 | 6.45–6.85(1H) |
| | | | | | | | | | 1190 | 7.00–7.30(4H) |
| | | | | | | | | | | 7.90(1H) 8.20(1H) |
| 17 | (204) | —CF₃ | Cl | =N— | —CH₃ | H | —C₄H₉ | —C₄H₉ | 3250 | 0.80–1.10(6H) |
| | | | | | | | | | 1670 | 1.10–1.80(8H) |
| | | | | | | | | | 1500 | 1.60(3H) |
| | | | | | | | | | 1460 | 3.58–3.90(2H) |
| | | | | | | | | | | 3.87–4.27(4H) |
| | | | | | | | | | 1320 | 4.70(1H) |
| | | | | | | | | | 1190 | 6.63–7.27(5H) |
| | | | | | | | | | | 7.90–8.23(2H) |
| 18 | (205) | —CF₃ | Cl | =N— | —CH₃ | —CH₂CH₃ | —C₂H₅ | —C₂H₅ | 1250 | 0.70–1.80(14H) |
| | | | | | | | | | 1680 | 3.80–4.40(5H) |
| | | | | | | | | | 1500 | 4.70(1H) |
| | | | | | | | | | 1460 | 6.20–6.80(1H) |
| | | | | | | | | | 1320 | 7.00–7.25(4H) |
| | | | | | | | | | 1190 | 7.80(1H) 8.20(1H) |
| 19 | (206) | —CF₃ | H | =N— | H | H | —C₂H₅ | —C₂H₅ | 3250 | 1.33(6H) |
| | | | | | | | | | 1670 | 3.63–3.93(2H) |
| | | | | | | | | | 1500 | 3.90–4.37(4H) |
| | | | | | | | | | 1480 | 4.53(2H) |
| | | | | | | | | | 1330 | 6.77–7.27(6H) |
| | | | | | | | | | 1120 | 7.70–8.40(2H) |

TABLE 1-continued

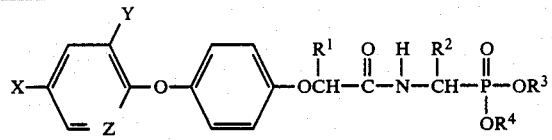

| Example | Compound No. | X | Y | Z | R¹ | R² | R³ | R⁴ | IR $\nu$(cm$^{-1}$) | NMR in CDCl$_3$ $\delta$(ppm) |
|---|---|---|---|---|---|---|---|---|---|---|
| 20 | (208) | —CF$_3$ | H | =N— | —CH$_3$ | H | —C$_2$H$_5$ | —C$_2$H$_5$ | 3250 1670 1500 1480 1330 1130 | 1.13–1.43(6H) 1.60(3H) 3.57–3.87(2H) 3.90–4.37(4H) 4.70(1H) 6.73–7.27(6H) 7.77–8.40(2H) |
| 21 | (210) | —CF$_3$ | H | =N— | —CH$_3$ | H | —C$_4$H$_9$ | —C$_4$H$_9$ | 3250 1670 1500 1480 1330 1130 | 0.80–1.13(6H) 1.13–1.83(8H) 1.60(3H) 3.60–3.90(2H) 3.87–4.37(4H) 4.70(1H) 6.83–7.27(6H) 7.80–8.40(2H) |
| 22 | (212) | H | —CF$_3$ | =N— | H | H | —C$_2$H$_5$ | —C$_2$H$_5$ | 3250 1670 1500 1430 1330 1240 | 1.33(6H) 3.63–3.93(2H) 3.90–4.33(4H) 4.53(2H) 6.80–7.27(6H) 7.87–8.27(2H) |
| 23 | (214) | H | —CF$_3$ | =N— | —CH$_3$ | H | —C$_2$H$_5$ | —C$_2$H$_5$ | 3250 1670 1500 1430 1330 1230 | 1.13–1.43(6H) 1.57(3H) 3.57–3.87(2H) 3.83–4.27(4H) 4.70(1H) 6.67–7.27(6H) 7.87–8.27(2H) |

FORMULATION EXAMPLE

One part of an active compound in accordance with this invention was added to 5000 parts of a mixture of acetone and water (1:1 by volume), and 2.6 parts of a nonionic surfactant (Sorpol 2680, tradename) to form a solution.

TEST EXAMPLE 1

Active compounds in accordance with this invention were formulated in accordance with Formulation Example above.

Test plants were those obtained by sowing seeds in soil and growing them for 2 to 3 weeks after emergence.

The formulations containing the active compounds of this invention were applied in predetermined dosages, and thereafter, the plants were grown for 3 weeks without applying the formulations. The results are shown in Table 2.

TEST EXAMPLE 2

Seeds of plants were sown in soil, and on the second day after sowing, treated as follows. The growth of the plants was then observed for 3 weeks.

The formulations prepared as above were applied uniformly to the surface of the soil after sowing in predetermined dosages, and then the plants were grown without applying the formulations. The results are shown in Table 3.

TABLE 2

| Compound No. | Rate of application (g/10a) | Plant | | | | | | | | | | | | | |
|---|---|---|---|---|---|---|---|---|---|---|---|---|---|---|---|
| | | A | B | C | D | E | F | G | H | I | J | K | L | M | N |
| (102) | 100 | 5 | 5 | 3 | 3 | 5 | 5 | 4 | 2 | 1 | 5 | | 0 | 0 | 0 |
| | 50 | 5 | 3 | 2 | 2 | 2 | 5 | 2 | 1 | 1 | 4 | | 0 | 0 | 0 |
| (106) | 200 | 4 | 3 | 4 | 4 | 3 | 4 | 3 | 2 | 2 | 3 | 5 | 0 | 0 | 0 |
| (108) | 100 | 5 | 5 | 5 | 5 | 5 | 5 | 4 | 4 | 5 | 5 | 5 | 0 | 0 | 0 |
| | 50 | 5 | 5 | 5 | 5 | 4 | 4 | 3 | 3 | 4 | 4 | 4 | 0 | 0 | 0 |
| (110) | 100 | 5 | 4 | 5 | 4 | 3 | 3 | 3 | 3 | 3 | 3 | | 0 | 0 | 0 |
| (200) | 200 | 4 | 3 | 4 | 4 | 3 | 4 | 3 | 2 | 2 | 3 | | 0 | 0 | 0 |
| (202) | 100 | 5 | 5 | 5 | 5 | 4 | 5 | 5 | 5 | 5 | 5 | | 0 | 0 | 0 |
| | 50 | 5 | 4 | 4 | 4 | 3 | 4 | 4 | 4 | 4 | 4 | | 0 | 0 | 0 |
| (204) | 100 | 5 | 3 | 4 | 4 | 3 | 3 | 3 | 3 | 3 | 3 | | 0 | 0 | 0 |
| (208) | 100 | 5 | 3 | 4 | 4 | 3 | 4 | 4 | 3 | 3 | 3 | | 0 | 0 | 0 |
| (210) | 100 | 5 | 4 | 5 | 4 | 3 | 5 | 4 | 3 | 3 | 3 | | 0 | 0 | 0 |
| (105) | 100 | 5 | 4 | 3 | 3 | | | 3 | | | | | 0 | 0 | 0 |
| (111) | 100 | 5 | 4 | 3 | 3 | | | 4 | | | | | 0 | 0 | 0 |
| (203) | 100 | 5 | 4 | 3 | 3 | | | 4 | | | | | 0 | 0 | 0 |
| (205) | 100 | 5 | 4 | 4 | 4 | | | 4 | | | | | 0 | 0 | 0 |

TABLE 3

| Compound No. | Rate of application (g/10a) | A | D | E | G | I | K | O | M | N |
|---|---|---|---|---|---|---|---|---|---|---|
| (102) | 100 | 5 | 5 | 4 | 5 | 3 | 5 | 3 | 0 | 0 |
|  | 50 | 4 | 4 | 3 | 4 | 2 | 5 | 2 | 0 | 0 |
| (104) | 50 | 5 | 5 | 5 | 5 | 4 | 5 | 3 | 0 | 0 |
| (202) | 50 | 5 | 5 | 5 | 5 | 5 | 5 | 3 | 0 | 0 |
| (105) | 100 | 5 | 4 |   |   |   | 2 | 2 | 0 | 0 |
| (111) | 100 | 4 | 4 |   |   |   | 2 | 2 | 0 | 0 |
| (203) | 100 | 5 | 4 |   |   |   | 2 | 2 | 0 | 0 |
| (205) | 100 | 5 | 4 |   |   |   | 3 | 2 | 0 | 0 |

The letters given in the column of "Plant" in Tables 2 and 3 represent the following plants.

A: *Digitaria adsendens*
B: *Eluesine indica*
C: *Setaria viridis*
D: *Setaria faberi*
E: *Echinochloa crus-galli*
F: *Poa annua*
G: *Sorghum halepense*
H: *Avena fatua*
I: *Agropyron repens*
J: *Panicum texanum*
K: *Amaranthus lividus*
L. Rice
M: Corn
N: Soybean
O: *Erigeron annuus*

What is claimed is:

1. A phenoxyalkanoylaminomethylphosphonic acid represented by the following formula (I)

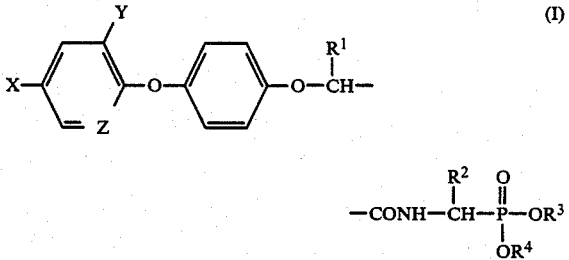

wherein X and Y are identical or different and each represents a hydrogen atom, a halogen atom, $CF_3$ or an alkyl group having not more than 5 carbon atoms, Z represents CH or N, and $R^1$, $R^2$, $R^3$ and $R^4$ are identical or different and each represents a hydrogen atom or a lower alkyl group having 1 to 5 carbon atoms.

2. A phenoxyalkanoylaminomethylphosphonic acid of claim 1 which is represented by the following formula (I)-A

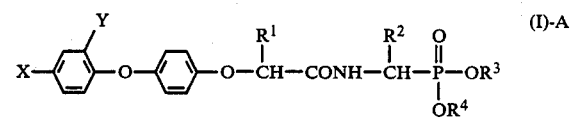

wherein X, Y, $R^1$, $R^2$, $R^3$ and $R^4$ are as defined in claim 1.

3. A phenoxyalkanoylaminomethylphosphonic acid of claim 1 which is represented by the following formula (I)-B

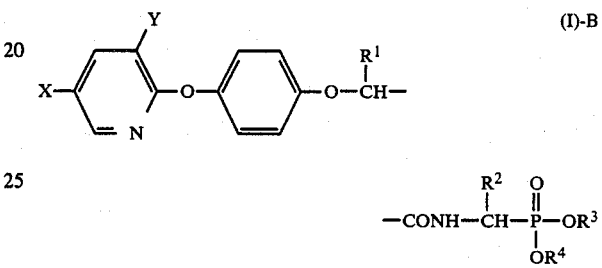

wherein X, Y, $R^1$, $R^2$, $R^3$ and $R^4$ are as defined in claim 1.

4. A method of eradicating weeds, which comprises applying the phenoxyalkanoylaminomethylphosphonic acid of formula (I) according to claim 1 to a locus where narrow-leaved weeds are growing or are likely to grow in an amount effective for eradicating the weeds.

5. The method of claim 4 wherein the locus is a locus where a crop is cultivated, and the crop is either a broad-leaved or narrow-leaved plant.

6. A herbicidal composition which comprises, as active ingredient, a herbicidally effective amount of a compound according to claim 1 and a carrier therefor.

7. The herbicidal composition which comprises, as active ingredient, a herbicidally effective amount of a compound according to claim 2 and a carrier therefor.

8. The herbicidal composition which comprises, as active ingredient, a herbicidally effective amount of a compound according to claim 3 and a carrier therefor.

* * * * *